United States Patent
Swider

(10) Patent No.: US 7,390,465 B2
(45) Date of Patent: *Jun. 24, 2008

(54) SYSTEM AND METHOD FOR CONTAMINATION DETECTION WITHIN SEALED CONTAINERS

(75) Inventor: John T. Swider, Port Crane, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 736 days.

This patent is subject to a terminal disclaimer.

(21) Appl. No.: 10/328,230

(22) Filed: Dec. 23, 2002

(65) Prior Publication Data

US 2007/0183927 A1 Aug. 9, 2007

Related U.S. Application Data

(63) Continuation-in-part of application No. 10/314,631, filed on Dec. 9, 2002, which is a continuation-in-part of application No. 10/201,169, filed on Jul. 22, 2002.

(60) Provisional application No. 60/358,577, filed on Feb. 21, 2002, provisional application No. 60/344,847, filed on Dec. 31, 2001, provisional application No. 60/344,848, filed on Dec. 31, 2001, provisional application No. 60/340,118, filed on Dec. 10, 2001.

(51) Int. Cl.
*G01N 33/00* (2006.01)
(52) U.S. Cl. ............... 422/119; 422/83; 436/1; 436/2; 436/86; 436/104; 73/23.2; 73/37
(58) Field of Classification Search ............. 422/119
See application file for complete search history.

(56) References Cited

U.S. PATENT DOCUMENTS

| | | | |
|---|---|---|---|
| 3,661,256 A | * | 5/1972 | Hain .............. 209/645 |
| 3,915,339 A | | 10/1975 | Matson |
| 3,998,101 A | | 12/1976 | Fagan et al. |
| 4,580,440 A | | 4/1986 | Reid et al. |
| 4,718,268 A | | 1/1988 | Reid et al. |
| 4,764,351 A | | 8/1988 | Hennebert et al. |

(Continued)

FOREIGN PATENT DOCUMENTS

WO   97/06106   *  2/1997

OTHER PUBLICATIONS

U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

*Primary Examiner*—Lyle A. Alexander
(74) *Attorney, Agent, or Firm*—Burns & Levinson LLP; Jacob N. Erlich; Harvey Kaye

(57) ABSTRACT

A system and a method to detect biological and chemical agents in a sealed contained at, for example, a mail-processing center. The system includes filtration and vacuum subsystems cooperatively working to draw an air sample from the interior of the particulate containment system for evaluation by a biosensor or chemical analyzer to detect the presence of a contaminant. The vacuum subsystem includes a vacuum generator, flow meters, and pressure regulators to accommodate the varying volume within the particulate containment system. The filtration system includes an inlet filter and a high efficiency particle air filter (HEPA) filter. The inlet filter removes coarse impurities, such as dust and dirt, from the incoming air to improve sensor efficiency. The HEPA removes contaminants from the air sample prior to being released to the surrounding environment, thereby eliminating the possibility of spreading the contamination outside the particulate containment system. Additionally, an agitating means is connected to the particulate containment system to loosen contaminants and create a contaminated air cloud, thereby increasing the concentration of contaminants in the interior.

14 Claims, 6 Drawing Sheets

U.S. PATENT DOCUMENTS

| | | |
|---|---|---|
| 4,987,767 A | 1/1991 | Corrigan et al. |
| 5,109,691 A | 5/1992 | Corrigan et al. |
| 5,255,556 A | 10/1993 | Lobdell .................... 73/31.02 |
| 5,322,603 A | 6/1994 | Kameda |
| 5,345,809 A | 9/1994 | Corrigan et al. |
| 5,465,607 A | 11/1995 | Corrigan et al. |
| 5,470,546 A | 11/1995 | Hall |
| 5,585,575 A | 12/1996 | Corrigan et al. |
| 5,591,117 A | 1/1997 | Zelno |
| 5,700,426 A | 12/1997 | Schmitthaeusler et al. |
| 5,841,038 A | 11/1998 | Volz |
| 5,859,362 A | 1/1999 | Neudorfl et al. |
| 5,942,699 A | 8/1999 | Ornath et al. |
| 6,074,608 A | 6/2000 | Matz .......................... 422/83 |
| 6,159,422 A | 12/2000 | Graves et al. |
| 6,183,950 B1 | 2/2001 | Madonna et al. |
| 6,295,860 B1 | 10/2001 | Sakairi et al. |
| 6,324,927 B1 | 12/2001 | Ornath et al. |
| 6,742,703 B2 | 6/2004 | Esakov et al. |
| 6,792,795 B2 * | 9/2004 | Jones et al. .................... 73/37 |
| 2001/0029793 A1 | 10/2001 | Moler et al. ............. 73/863.22 |
| 2002/0124664 A1 | 9/2002 | Call et al. |
| 2002/0126008 A1 | 9/2002 | Lopez et al. |
| 2003/0086821 A1 | 5/2003 | Matthews .................... 422/29 |
| 2003/0136179 A1 * | 7/2003 | Felice et al. ............... 73/31.03 |
| 2003/0222132 A1 | 12/2003 | Esakov et al. |

* cited by examiner

SYSTEM AND METHOD FOR CONTAMINATION DETECTION WITHIN SEALED CONTAINERS

CROSS-REFERENCE TO RELATED APPLICATIONS

This invention claims priority of:

Utility application Ser. No. 10/314,631, "MAIL TUB WITH AIR PORTS," filed Dec. 9, 2002, Provisional Application Ser. No. 60/344,848, "CLOSED LOOP SYSTEM FOR AIR SAMPLING OF CONTAINED MAIL PRODUCTS" filed Dec. 31, 2001, and utility application Ser. No. 10/201,169 filed Jul. 22, 2002;

Provisional Application Ser. No. 60/344,847, "SYSTEM AND METHOD FOR CONTAMINATION DETECTION WITHIN A SEALED CONTAINER," filed Dec. 31, 2001, and Provisional Application Ser. No. 60/358,577, "METHOD AND SYSTEM FOR AUTOMATED HAZARDOUS MATERIAL DETECTION," filed Feb. 21, 2002. All the above-mentioned provisional applications are hereby incorporated by reference.

FIELD OF THE INVENTION

This invention relates generally to the containment, sensing and neutralizing of hazardous material in or on articles in an enclosure, and, more particularly to the containment within a controlled space of a biological agent or other hazardous material or the like disposed in or on an article, such as a piece of mail.

BACKGROUND OF THE INVENTION

The recent incidents of anthrax-laced letters being transported through the United States Postal Service (USPS) facilities to unsuspecting recipients has alarmed the nation and the world. Currently, the tainted letters are discovered after the recipient accepts delivery or by alert postal employees noticing white powder that could be anthrax on mail parcels or pieces, sorting and distribution equipment, or themselves. There appears to be no current security devices or procedures that are available to intercept such letters at the earliest source of introduction into the USPS system, for example at the mailbox or post office drop box or mail collection tub, or upon entry into a sorting facility or sorting system to test them for hazardous material, and to neutralize such material when it is found.

Currently when there is suspicious mail, it is all bulk irradiated as was done during the recent anthrax problem thereby delaying some mail for months and damaging or destroying some of the mail due to problems caused by the irradiation. For example some of this irradiated mail became brittle and pieces broke off.

Almost all mail articles at one time or another are collected and transported to postal facilities by way of mail tubs. Therefore, mail tubs can be the first point of containment if a hazardous material is detected prior to the exposure of its air and contents at a postal facility.

Mail is also distributed in large trucks such as tractor/trailers, and this provides another opportunity to detect hazardous material on or in the mail.

Some mail tubs have lids or covers, but they are not airtight vessels. Mail articles that contain hazardous material within or on the outer surface contaminate not only the other mail articles within the mail collection tub, but also the mail collection tub air. The agitation of the mail collection tub in transport or by routine handling by the postal employees can cause the hazardous material to form a plume or aerosol. There is also a threat of contaminating postal employees by inhaling the contaminated air as well as by direct contact to skin tissue.

SUMMARY OF THE INVENTION

The present invention provides systems and sub-systems, and parts thereof for containing the mail at the earliest opportunity (or somewhere down the distribution line) determining whether there is hazardous material present on or in the mail, removing the mail that has hazardous material detected, from the normal distribution/sorting system, and neutralizing the hazardous material.

In accordance with the present invention there is a particulate containment system capable of being connected to a biohazard detection system for analysis of the contents within the particulate containment system. Additionally, the particulate containment system can be attached to an agitation system that disturbs particulates settled on objects within the particulate containment system. An air stream can be formed within the particulate containment system to transport the disturbed particulates to an air outlet connected to the biohazard detection system. This can be, for example, by creating an air cloud with the particulate contained therein.

Agitation may be provided in various manners, including by using air currents to do so, although many embodiments also rely upon physical agitation in addition to any air currents which may be used.

One embodiment of the particulate containment system is equipped with one-way valves to seal the air within a container and which are capable of being connected to a closed-loop or an open-loop biohazard detection system for air sample evaluation. Air is drawn out of the particulate containment system by the biohazard detection system equipped with a mechanism for causing air flow, such as a fan to provide positive pressure, or a vacuum to provide negative pressure. The one-way valves, or dripless quick disconnect couplings which could be used instead of the one-way valves, will open when subjected to a predetermined positive pressure (discussed in detail below). The number of valves is determined by the size of the container.

An embodiment of the particulate containment system may include a substantially rigid container having, a bottom, and sides with generally perpendicularly aligned walls forming a chamber, a rim defining an open top, and a lid. The lid is configured to substantially form an airtight seal when engaged with the rim. There is an air inlet that may automatically open to draw air into the chamber and which prohibits air from exiting the chamber. There may be an air outlet that may automatically open to exhaust air from the chamber and prohibit air from entering into the chamber, or dripless quick disconnect couplings may be used. Thereby, fresh or recirculated air is drawn into the chamber by at least one one-way inlet and potentially contaminated air is drawn out of the chamber by at least one one-way outlet to allow for sampling for possible biological or other hazardous material contamination. Other embodiments of automatic air inlets and outlets include manually operated mechanisms and plugs.

Another feature of the container may include and arrangement for raising the mail from the bottom of the container, such as by using standoffs along the bottom of the container to facilitate airflow movement through the chamber when the lid is engaged to the rim of the container and, for example, a vacuum source is applied to at least one one-way outlet. The standoffs elevate mail articles above the bottom of the container, thereby creating a space where solid particulates, including contaminates, may settle. When air passes through the space, an air stream disturbs the solid particulates causing an increase in the concentration of particulates in the air stream and, thereby increasing the probability of detection of contamination by the biohazard detection system. Alternatives to the standoffs includes a mesh screen insert having legs made of suitable material such as wire or plastic or a subfloor with openings located above the bottom.

A further feature which may be used in the particulate containment system includes channels along the walls of the container to facilitate airflow movement through the chamber similar to the raised standoffs mentioned above in order to permit flow of air and particulates.

The particulate containment system can be attached to an agitation system to loosen particulates to further increase the concentration of contaminants in the chamber to facilitate air sampling. The agitation system can include a pneumatic or hydraulic cylinder, and linear and/or rotary actuator.

Agitation mechanisms may be used in a continuous system in which the containers are temporarily halted from their forward motion to be agitated, and during or after which the air is sampled, after which the containers continue their travel.

For a better understanding of the present invention, together with other and further objects thereof, reference is made to the accompanying drawings and detailed description.

DETAILED DESCRIPTION OF THE PREFERRED EMBODIMENTS

Figure 1:
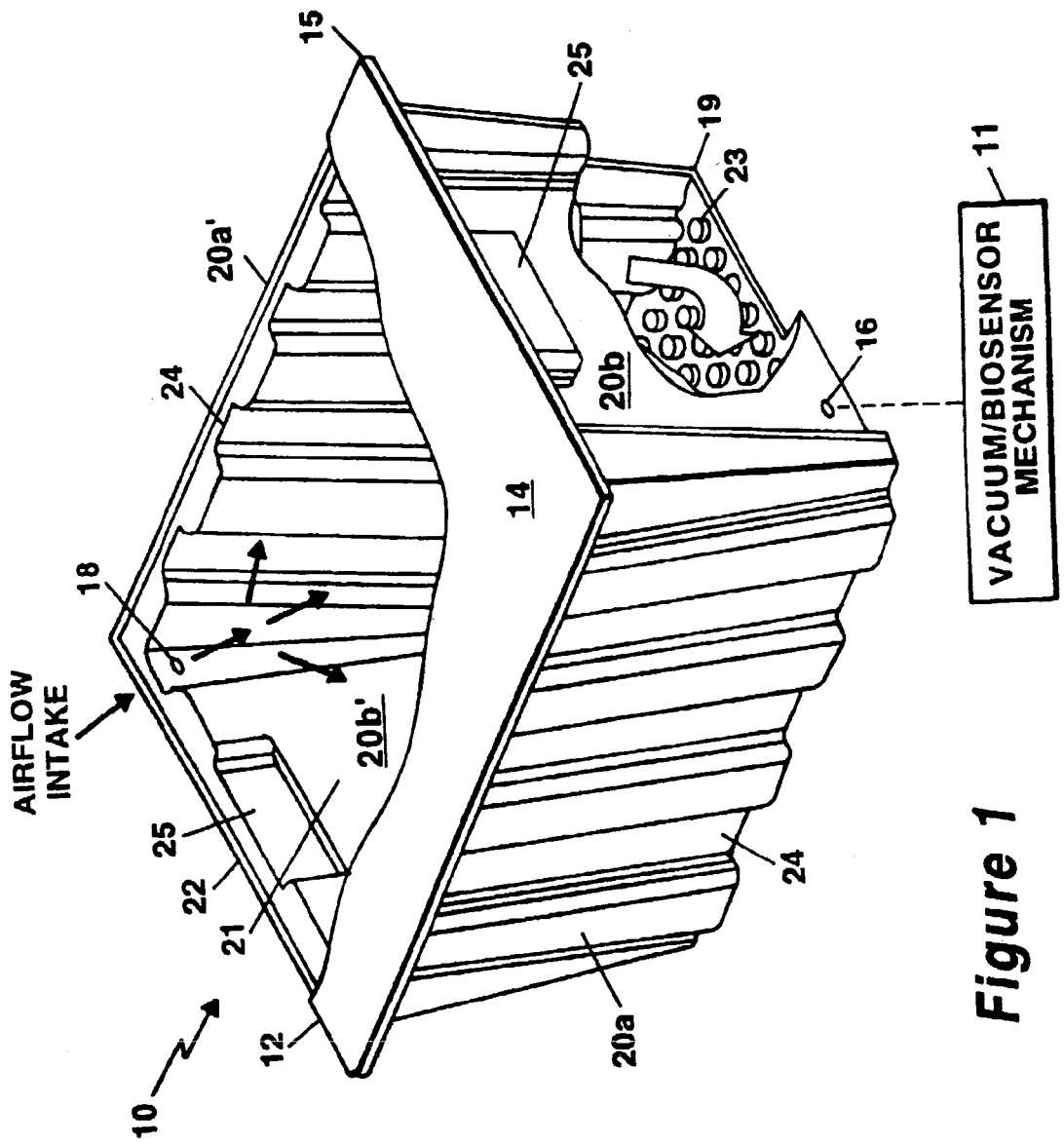
FIG. 1 is an isometric view of a mail container system illustrating airflow intake and circulation, and a schematic representation of such system cooperating with a vacuum or air/biosensor mechanism.

FIG. 1 shows a particulate containment system 10 usable with the present invention which includes a substantially rigid container 12 and having a lid 14. An air outlet 16 and an air intake 18 are provided in container 12 for sampling air in the particulate containment system 10 for prohibited and possibly hazardous material including biological contamination, such as anthrax, and explosives An embodiment of the container 12, when it is a mail tub, includes a bottom wall 19, sidewalls 20a, 20a', end walls 20b, 20b', a lip 22 forming an open end 21, and molded standoffs 23 along the bottom wall 19. The container 12 may be a unitary molded structure made of any substantially rigid material, examples of which include plastic, rubber, and metal. Vertical channels 24 add strength to the container 12 and assure an unobstructed path for any particulates to travel to the air outlet 16 when a vacuum or like is applied to air outlet 16 or blower or like is applied to air intake 18. Additionally, the two opposing end walls 20b, 20b' include handhold indentations 25 near the open end 21 for lifting the container 12. The interior and exterior of the container 12 are configured to nest one container within another container for storage. For this purpose, the four walls may be constructed to narrow slightly from the top toward the bottom.

Figure 2:
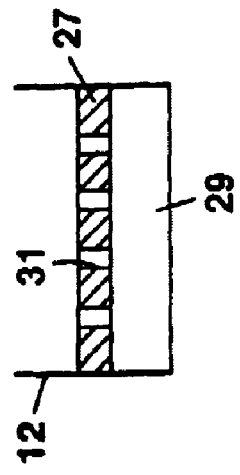
FIG. 2 is partial sectional view of the lid and container rim usable in the FIG. 1 container and other embodiments of the present invention.

In the particulate container 12, a lid 14 is provided which is suitably sized and contoured to tightly fit about the lip 22 of container 12, as illustrated in FIG. 2. The lid 14 is preferably a unitary molded, generally rectangle structure made of any substantially rigid material, examples of which include plastic and rubber, which is of a sufficient width and length to extend longitudinally outwardly over the lip 22 of container 12. The edge 15 of the lid 14 is, for example, a C shape configuration forming a substantially airtight seal with the lip 22 of the container 12 and is independent of pressure.

Figure 3A:
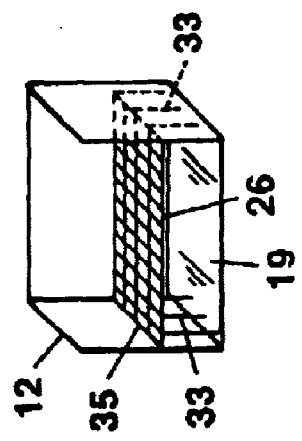
FIG. 3A is a schematic cross-section view of a mesh insert usable in the FIG. 1 container and other embodiments of the particulate containment system.
Figure 3B:
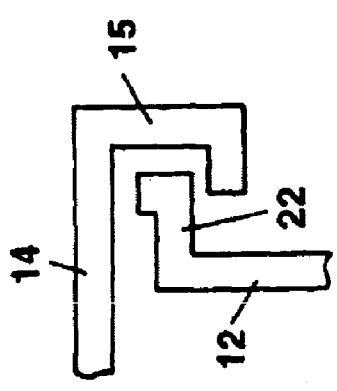
FIG. 3B is a schematic cross-sectional view of a subfloor with holes.

The molded standoffs 23 (FIG. 1) prevent mail articles from resting directly on the bottom wall 19 of the container 12 and assures an unobstructed path for any particulates to travel to the air outlet 16 when a vacuum or like is applied. Additionally, the molded standoffs 23 add strength to the container 12. An alternative to molded standoffs 23 or protrusions is a mesh insert 26 having legs 33 that raise the mesh structure 35 above the bottom wall 19, as illustrated in FIG. 3A. The mesh insert 26 can be made of any suitable material, such as wire or plastic, that has sufficient strength and durability. A second alternative to molded standoffs 23 is a subfloor 27 with perforations or holes 31, illustrated in FIG. 3B. The mesh insert 26 and subfloor 27 each provides a settling area 29 for loose particles from the objects to collect for the detection process. In either construction the vertical channels 24 extend down below the mesh insert 26 or subfloor 27.

The container 12 (FIG. 1) preferably includes air intake 18 and air outlet 16 that can be arranged to be automatically opened when coupled to the biohazard detection system 11 with a negative or positive pressure device, such as a vacuum or blower or fan. The biohazard detection system can be a closed-loop system or open-loop system. The air intake 18 and air outlet 16 may be self-sealing when not attached to, for example, the biohazard detection system 11. The attachment of the biohazard detection system 11 will automatically open the air intake 18 and air outlet 16 to allow air samples to be drawn from the container 12. The air intake 18 and air outlet 16 may be similar to air chucks on a compressed air system.

The air vent 18 can be located anywhere on container 12, but is preferred on an end wall 20b near the top open end 21. Similarly, the vacuum port 16 can be located anywhere on container 10, but is preferred on the opposing end wall 20b of the air vent 18 and near the bottom wall 19 of the container 12. The preferred locations are advantageous because air is drawn from the top of the container 10 where high concentration airborne contaminants are likely. Additionally, contaminants that settle on the bottom 19 will also by drawn from the container 10 as air travels to the vacuum port positioned the bottom wall 19.

In another embodiment, the air intake 18 and the air outlet 16 operate based on pressure differential. One-way valves may be installed within the air outlet 16 and air intake 18 for automatic closure to seal the interior of the particulate containment system 10 when vacuum is not applied, thereby assuring contaminants do not migrate into the surrounding environment. Another manner of accomplishing this is to use a HEPA filter which air is drawn through before exiting the container so that no contaminants can exit the container. For illustration purposes, examples of the above-mentioned valves are provided below.

EXAMPLE 1

Air can be forced into the container 12 by an air supply line connected to the air intake 18. In this case, the pressure within the container 12 is more than the pressure on the outside of the container 12 or on the high-pressure side of the air intake 18. Therefore, the air intake 18 opens when the pressure applied by the air supply reaches a pre-determined pressure differential level between the container internal pressure and the pressure outside the container. Once the air intake 18 opens, the pressure within the container 12 begins to rise. The air outlet 16 opens when the container pressure reaches a level greater than a predetermined level. The container air can now freely flow to the bio-detection system for analysis.

EXAMPLE 2

The air can be drawn out of the container 12 by a vacuum line connected to the air outlet 16. In this case, the pressure within the container 12 is less than the pressure on the outside of the container 12 or on the low-pressure side of the air outlet 16. Therefore, the air outlet 16 will open when the pressure applied by the vacuum decreases to a pre-determined level. Once the air outlet 16 opens, the pressure within the container 12 begins to drop and becomes lower than the pressure on the outside of the container or on the high-pressure side of the air intake 18. Therefore, the air intake 18 will open when the container pressure reaches a predetermined level. The container air can now freely flow to the bio-detection system for analysis.

In a further embodiment of the particulate containment system 10, the air intake 18 and air outlet 16 are simple port holes that are plugged with stoppers (not shown) sized to tightly fit within the port holes. Since the closure of the holes allows for the possibility of air leaking or migrating out of the container 12 while the stoppers are being installed, the operator may allow sufficient time to elapse after air sampling before disconnecting, for example the bio-detection system, from the holes, thereby maintaining the integrity of the air quality of the surrounding environment. Such a time delay will allow the particulates concentrated in the disturbed air to settle and the container pressure to stabilize to approximately ambient pressure. Once the air currents have sufficiently stopped within the container 12, then the bio-detection system can be disconnected and stoppers inserted in the port holes. Now the container 12 can be transported safely to the next processing station.

Figure 4C:
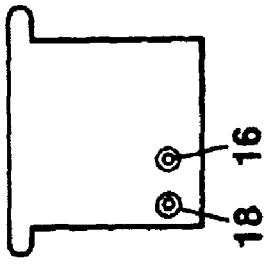
FIGS. 4A-4C are schematic cross-sectional views of alternative air intake and air outlet embodiments usable in the FIG. 1 container and other embodiments of the particulate containment system.
Figure 4B:
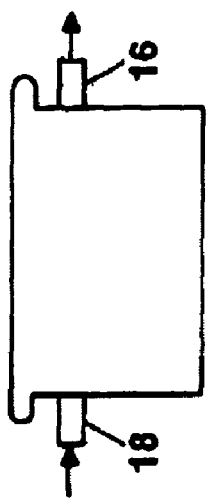
Figure 4A:
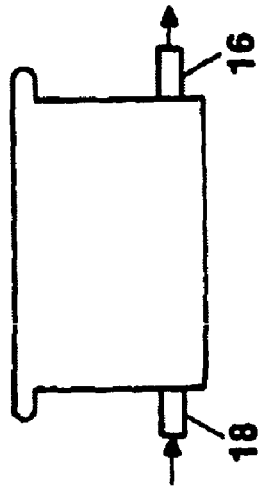
Figure 4D:
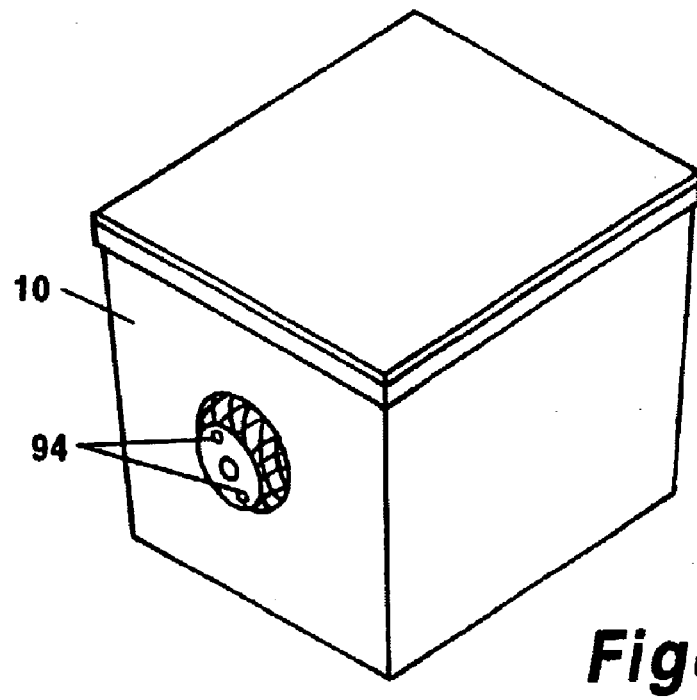
FIG. 4D is an isometric view similar to FIG. 1, showing a containment system in which valves are mounted into openings in the side thereof.

In additional embodiments of the particulate containment system 10, air intake 18 and air outlet 16 are a combination of three embodiments described above. For example, an automatic opening device in combination with a pressure sensitive opening device or an automatic opening device in combination with a stopper device or a pressure sensitive opening device with a stopper device. The combinations are interchangeable with the air intake 18 and the air outlet 16. One such arrangement is shown in FIG. 4D. The air intake 18 can be located anywhere on container 12, but is preferred on an end wall 20b near the top open end 21, as illustrated in FIG. 1. Similarly, the air outlet 16 can be located anywhere on container 12, but is preferred on the opposing end wall 20b of the air intake 18 and near the bottom wall 19 of the container 12, as illustrated in FIG. 1. The preferred locations are advantageous because air is drawn from the top of the container 12 where high concentration airborne contaminants are likely. Additionally, particulates that settle on the bottom 19 will also by drawn from the container 12 as air travels to the air outlet positioned the bottom wall 19.

Alternative embodiments of the particulate containment system 10 can position air intake 18 and air outlet 16 along substantially the same horizontal plane in a sidewall of a container. There are many possible embodiments. One such embodiment for illustrations purposes is along a lower horizontal plane of the container near the bottom, as illustrated FIG. 4A. In this case, the largest concentration of particulates is along the bottom and blowing or drawing air through this portion of the container may result in the maximum probability of detecting a contaminant. A second location is near the top of the container to analyze a plume of highly concentrated particulates, as illustrated FIG. 4B. A third location is along a lower horizontal plane but in the same wall, as illustrated in FIG. 4C. The optimal location for the air intake 18 and the outlet 16 is determined by the system used to sample the air from within the container 12. FIG. 4D shows a container having a construction somewhat similar to the one shown in FIG. 1. However, there are openings in opposite sides which contain valves which assist in the operation.

When a vacuum pump is used, air may pass from the outside environment into the vacuum mail tub 10 through air vent 18 into the mail tub 10. The air exits through the vacuum port 16 when a commercially available vacuum with a biological agent sensor attachment (not shown) is attached to vacuum port 16. The air samples from the mail tub 10 are analyzed to detect a biological agent or other contaminant. If such a contaminant is detected, the vacuum port 16 and the air vent 18 can be plugged with self-sealing plugs (not shown) to seal the contaminant in the mail tub and be transported to a decontamination center for further processing. If desired HEPA filters may be used for this purpose.

Figure 5:
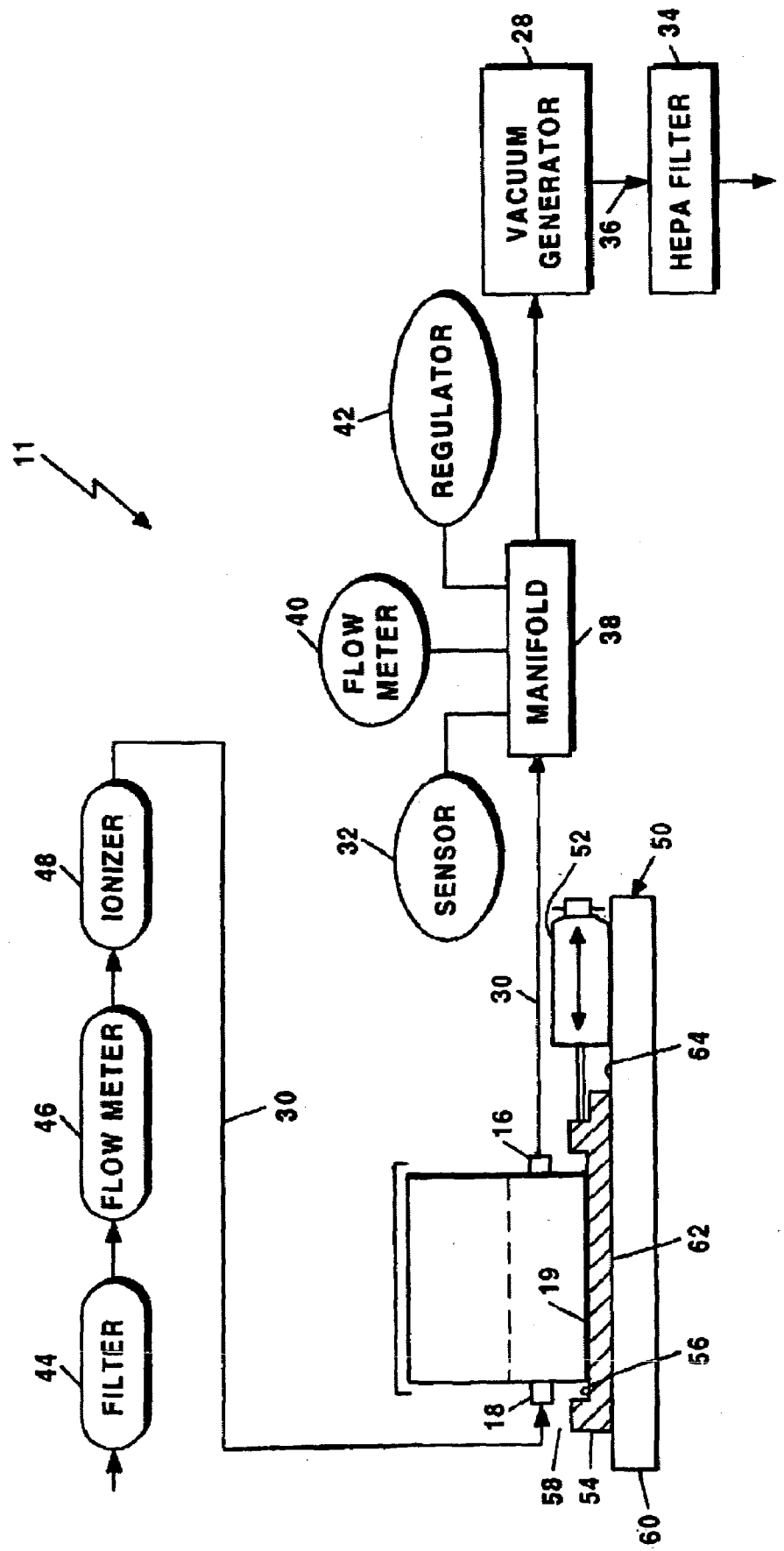
FIG. 5 is a schematic view of one type of agitation and air system.

The particulate containment system 10 and the embodiments thereof can be connected to a biohazard detection system 11 that agitates the contents of the particulate containment system 10. The particulate containment system 10 can be further enhanced to accommodate special fixturing to secure the particulate containment system 10 to the agitation system, such as by locating pin holes 94 (See FIG. 4D) to receive locating pins of the agitation system for alignment and agitation purposes. One such biohazard detection system 11 is illustrated in FIG. 5.

This embodiment of the biohazard detection system 11 includes a vacuum generator 28 and an air duct system 30 connected to an air outlet 16 of the particulate containment system 10, which includes the container or tub 12. The tub 12 also includes an air intake 18 to which the air duct system 30 can be connected to form a vent system to draw air out of the tub 12 for analysis. A sensor 32 is connected to the air duct system 30 between the air outlet 16 and the vacuum generator 28. The sensor 32 can be one or more conventional sensors capable of detecting biological and chemical contaminants, such as anthrax or small pox, explosives or some other type of hazardous material. A high efficiency particle air filter (HEPA) 34 is attached to the outlet 36 of the air duct system 30 to filter out contaminants before being exhausted into surrounding atmosphere.

The vacuum which is used to draw air through the tub 12 is produced using compressed air created by the vacuum generator 28 or material transfer pump. The vacuum pulls the air through a manifold 38, which can house the sensor 32. The manifold 38 also can house a flow meter 40 and regulator 42 to adjust the air flow as required to match the tub 12 size and the density of the materials (such as loose filled or densely packed) inside the tub 12.

The biohazard detection system 11 includes an inlet air filter 44, inlet flow meter 46 and an ionizer 48 connected to the air duct system upstream of the particulate containment system air intake 18. Air being drawn from outside is rough filtered by the inlet air filter 44 to remove dust and large particles. The inlet flow meter 46 assures the appropriate air mass enters the air duct system 30. The ionizer 48 removes the static electric charge from the air to help eliminate static electricity inside the tub 12, thereby facilitating better movement of particles into the air stream. This embodiment of the biohazard detection system 11 is shown with all three components connected to the air duct system 30. However, alternative embodiments are envisioned that include only one or two or none of the above-mentioned components depending on the system specification.

Figure 6:
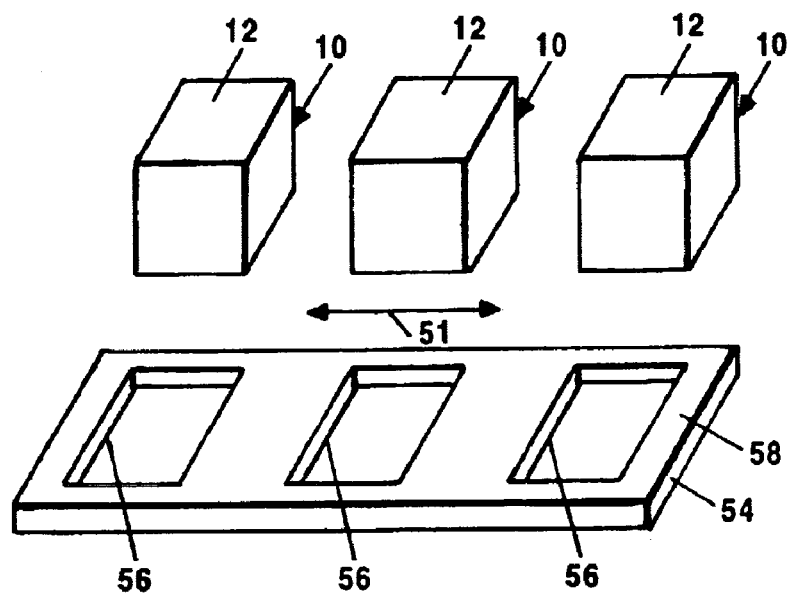
FIG. 6 is a schematic isometric view of an agitation tray usable in the FIG. 5 agitation system.

The tub 12 or other particulate containment system is capable of being attached to a particulate agitation system 50 to loosen contaminants within the particulate containment system 10. The particulate agitation system 50 can be of any mechanical or electrical mechanism that disturbs particulates contained on or in objects within the particulate containment system 10 including rotation and linear movement. One embodiment of the particulate agitation system 50 provides a linear back and forth motion as indicated by arrow 51 in FIG. 6 causing the tub contents to mix and collide with each other in a non-destructive manner, thereby shaking loose the contaminants from the contents. Some of the contaminants will settle on the floor 19 of the tub 12. The agitation can be achieved pneumatically with the use of air cylinder(s) 52 or electrically with an electronic linear actuator or hydraulically with a hydraulic cylinder. Each method is adjustable for length of stroke and speed/cycle time. Once the contents of the tub 12 are in motion or sufficiently agitated, air pressure or vacuum can be used to transfer suspended particles to the sensor 32. The particulate agitation system 50 includes an agitation tray 54 connected to the air cylinder(s) 52.

The agitation tray 54 includes one or more recesses 56 on a top surface 58 to seat the tubs 12. The agitation tray 54 is made of suitable material, such as metal, plastic or wood. The recesses 56 are of sufficient depth, length and width for the tub 12 to seat securely during agitation without the use of a locking device. However, alternative embodiments may include a locking device (not shown).

The air cylinders 52 are fixedly attached to an agitation base 60 and the agitation tray 54 is in moveable contact with the agitation base 60. The moveable relationship between the agitation tray 54 and the agitation base 60 can be created by many different embodiments known to those skilled in the art. For example, the agitation tray 54 can include conventional wheels or the agitation base 60 can include conventional conveyor rollers. Alternatively, the agitation tray 54 and agitation base 60 can be made of complimentary materials that have low contact friction allowing sufficient relative movement where the bottom surface 62 of the agitation tray 54 and top surface 64 of the agitation base 60 are in direct contact, and no rollers or wheels would be required.

Figure 8:
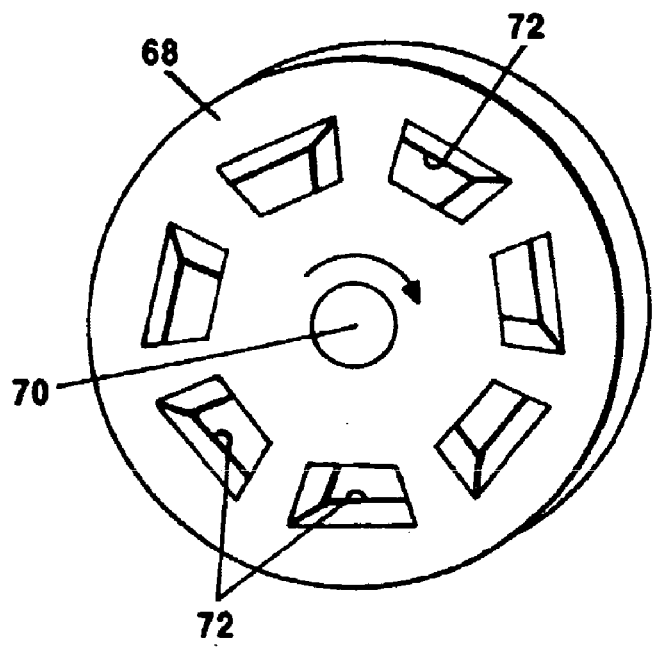
FIG. 8 is a schematic, pictorial representation of the rotary cylinder usable in the FIG. 7 agitation system and other embodiments of the agitation system.
Figure 7:
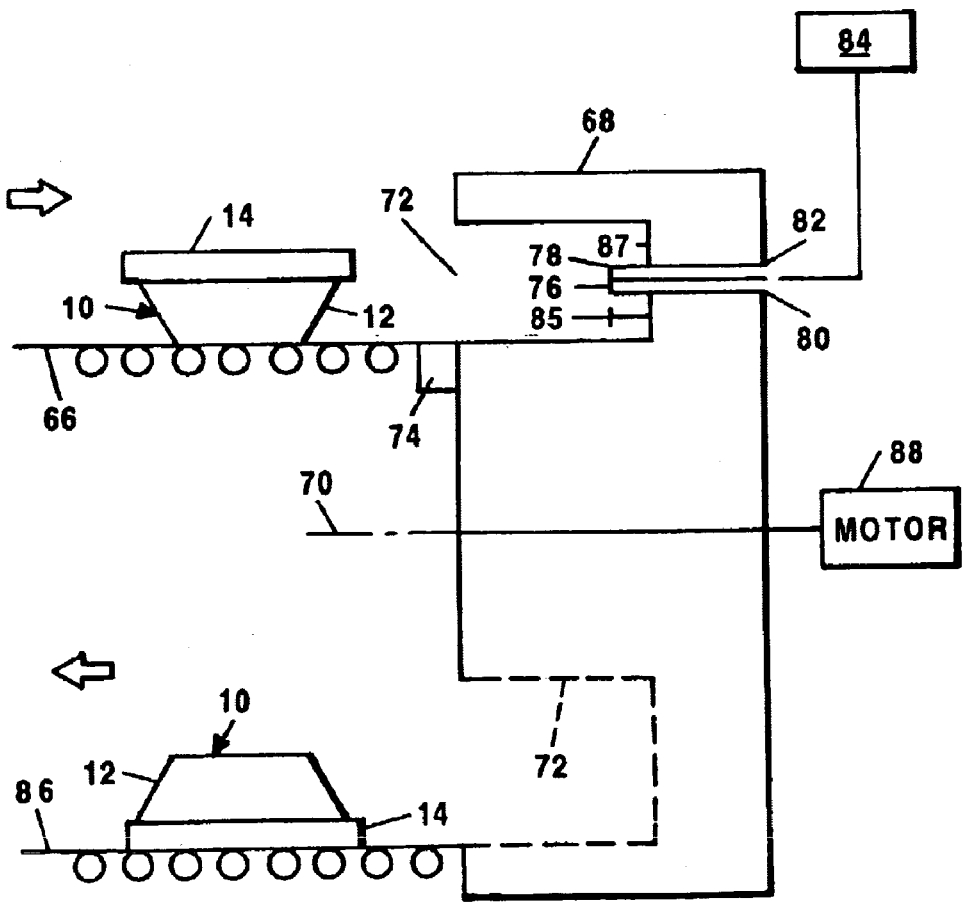
FIG. 7 is a schematic, cross-sectional side view of another type of agitation system showing a particulate containment system being fed into a chamber of a rotary cylinder and a particulate containment system being ejected from a chamber of the rotary cylinder.

Another embodiment of the particulate agitation system of the present invention is illustrated in FIGS. 7 and 8. The particulate containment system 10 is placed on an entrance roller conveyor 66 and transferred by the entrance roller conveyor 66 towards a rotary cylinder 68. The speed of the entrance roller conveyor 66 may be adjusted to ensure the productive capacity of the mail facility by allowing adjustment of the loading speed of the particulate containment systems 10 onto the entrance roller conveyor 66 and successive insertion of the particulate containment systems 10 into the rotary cylinder 68.

The rotary cylinder 68, located at the end of the entrance roller conveyor 66, rotates about a horizontal axis 70 and has a plurality of radially extending chambers 72, as shown in FIG. 8. A motor 88 drives and provides rotary motion to the rotary cylinder 68. Each radially extending chamber 72 is of sufficient depth, length, and width for a particulate containment system 10 to fit securely therein and is located on the rotary cylinder 68 such that alignment of each chamber 72 with the entrance roller conveyor 66 occurs. The particulate containment systems 10 (or tubs 12) are individually inserted into the chambers 72 in succession, each tub 12 being fed into a corresponding chamber 72 by a driving mechanism 74.

The driving mechanism 74 may be, for example, a pneumatic pusher capable of engaging the tubs 12 and dragging the tubs into the chamber 72 and then disengaging from the tubs 12. As the tubs 12 are fed into the chamber 72, the air outlet 16 and air intake 18 are aligned and engage onto respective air outlet mating nozzle 76 and air intake mating nozzle 78 within the chamber 72. The mating nozzles 76 and 78 are attached to a vacuum manifold 80 and air manifold 82, respectively, which are connected to an air sampling system 84. The mating nozzles 76 and 78 for both the air intake 18 and air outlet 16 may be located on the end wall 87 of the chamber 72. However, the mating nozzles 76 and 78 may be located on any wall of the chamber 72 and may be separately located on one or more walls depending upon the air outlet 16 and air intake 18 configuration of the tub 12 being used. Once the air outlet 16 and air intake 18 of the tubs 12 are engaged with the mating nozzles 76 and 78, the rotary cylinder 68 will index to the next position, allowing an empty chamber 72 to move into position at the end to the entrance roller conveyor 66 for the introduction of the next tub 12. Once the tub 12 is engaged with a chamber 72, the rotational cycle of the cylinder 68 provides for the rotation of the particulate containment system 10 thereby agitating the contents contained therein. Agitation of the contents is this manner allows, for example, the letters and mail parcels to mix and collide with each other in a non-destructive manner, but with enough force to loosen a portion of any contaminates contained therein or thereon to create a contaminated air cloud, thereby increasing the concentration of contaminants in the interior of the tubs 12 to facilitate air sampling.

After a predetermined interval and number of rotation cycles, sampling of the air within each tub 12 commences. Sampling may occur within each individual chamber 72 in succession or may occur simultaneously among all chambers 72. Rotary speeds of the cylinder 68 may be adjusted to ensure the productive capacity of the mail facility by allowing for successively engaging all chambers 72 within the rotary cylinder 68, sufficient agitation of the tubs 12, and air sampling of the particulate containment systems 10. This provides a synchronization, with minimum tolerance margins, of the steps for feeding the particulate containment systems 10 onto the entrance roller conveyor 66 and sampling of the air within each particulate containment system 10 contained in a chamber 72.

In one embodiment of the biohazard detection system 11, a vacuum subsystem is used for air sampling. Air passes from the outside environment into the particulate containment system 10 through the air manifold 82 and air intake mating nozzle 78 of the chamber 72 and air intake 18 into the particulate containment system 10. The air exits through the air outlet 16 when a commercially available vacuum system with an appropriate hazardous material sensor attachment is attached to the vacuum manifold 80 that connects to air outlet 16 of the tubs 12 via the air outlet mating nozzle 76 of the chamber 72. The air samples from the particulate containment system 10 are analyzed to detect contaminants. If such a contaminant is detected, the tub 12 is transported to a decontamination center for further processing.

Tubs 12 in which no contamination is detected are ejected from the chamber 72 by a chamber ejection mechanism 85 onto an exit conveyer belt 86 that will feed the particulate containment system 10 downstream for further standard processing. In one embodiment, the chamber ejection mechanism 85 is a pneumatic pusher capable of engaging the tub 12 and pushing the tub out of the chamber 72 and onto an exit roller conveyer 86. In the embodiment shown in FIG. 7, the tub 12 is ejected onto the exit roller conveyer 86 upside down (i.e., lid 14 in contact with the exit roller conveyer 86) such that the container 12 may be separated from the lid 14 thereby allowing the letters and mail parcels contained within the particulate containment system 10 to drop onto the exit roller conveyer 86 and fed to other automation or culling/sorting areas.

Figure 9:
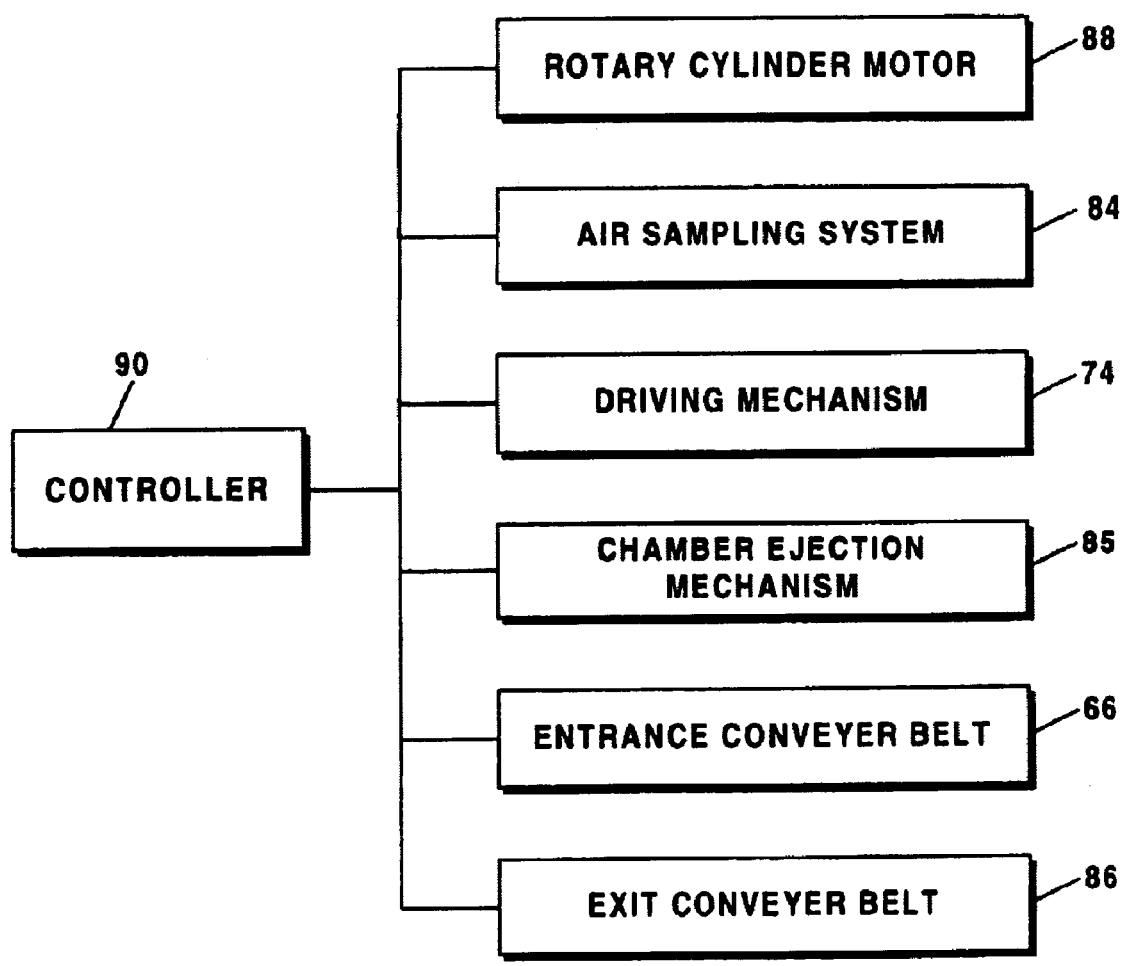
FIG. 9 is a schematic block diagram of the control system usable in the FIGS. 7 and 8 agitation system and other embodiments of the agitation system.

An example of an implementation of the controller 90 with a biohazard detection system is illustrated in FIG. 9 where the controller 90 is operably connected to the biohazard detection system 11 of FIG. 7. The controller 90 can also be integral to a mail processing/sorting system.

In another embodiment of the biohazard detection system 11, a neutralizing agent can be introduced into a tub 12 found to be contaminated through, for example, the air intake 18 in order to decontaminate the contents of the tub 12 while the tub is still located within the chamber 72.

In one embodiment, multiple rotary cylinders 68 may be installed within the mail processing center, each having a diverting conveyor system for contaminated mail tubs so as not to impede mail flow requirements.

The preferred and alternative embodiments of the biohazard detection systems 11 are capable of being operably connected to a controller 90 or like to sequence tasks and control the functions of the systems 11, such as motors, actuators, sensors, fans, vacuums, blowers, and conveyor belts It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A system for detecting biological and chemical agents in an article processing system, comprising:
    a. means for moving sealed containers in which articles are disposed;
    b. means for agitating such containers to loosen contaminants which may be contained therein or thereon and create a contaminated air cloud to increase the concentration of such contaminants in the air in the sealed containers to facilitate air sampling;
    c. means for making a temporary connection to the sealed containers to withdraw air samples therefrom; and
    d. means for sensing any contaminants which are located in the air samples;
    said agitating means providing rotary movement to the containers and includes a rotating cylinder having radially extending chambers for holding the sealed containers.

2. A system as defined in claim 1, further comprising:
    e. means for providing coarse filtering of such air samples; and
    f. means for providing subsequent contaminant filtering of such air samples after they leave the means for providing coarse filtering.

3. A system as defined in claim 1, further comprising:
    a hazardous material sensor;
    a flow meter connection to said sensor;
    a regulator connected to said flow meter;
    said temporary connection means including a temporary connection from the sensor to a sealed container.

4. A system as defined in claim 3 wherein said temporary connection means includes a vacuum generator.

5. A system as defined in claim 1, further comprising:
    an air intake filter;
    a flow meter connected to said filter;
    an ionizer connected to said flow meter; and
    said temporary connection means including a temporary connection from the air intake filter to a seated container.

6. A system as defined in claim 5 further comprising:
    a hazardous material sensor;
    a flow meter connection to said sensor;
    a regulator connected to said flow meter;
    said temporary connection means including a temporary connection from the sensor to a sealed container and a vacuum generator.

7. A system as defined in claim 6, further comprising:
    e. means for providing coarse filtering of such air samples; and
    f. means for providing subsequent contaminant filtering of such air samples after they leave the means for providing coarse filtering.

8. A system as defined in claim 1, wherein said agitating means further includes an adjustable speed entrance conveyor for moving containers into said chambers, and means for indexing movement of the cylinder to another chamber when a container has been placed into a chamber to fill all chambers with containers.

9. A system as defined in claim 8 wherein said agitating means includes an exit conveyor for removing containers from the chambers.

10. A system as defined in claim 8 including means for taking air samples from the container individually and testing them for hazardous material.

11. A system as defined in claim 10 further comprising means for releasing those containers which are free of contaminated air to continue downstream for further processing and handling.

12. A method for detecting biological and chemical agents in or on articles, comprising the steps of:
    a. moving sealed containers in which articles are disposed;
    b. agitating such containers to loosen contaminants which may be contained therein and create a contaminated air cloud to increase the concentration of such contaminants in the air in the sealed containers to facilitate air sampling;

c. withdrawing air samples from the sealed containers; and d. sensing contaminants which are located in the air samples;

placing the containers into a rotating cylinder having radially extending chambers for holding the containers; and agitating the tubs during rotary movement thereof to release contaminants with the containers.

13. method as defined in claim 12, further comprising the steps of:

e. coarsely filtering such air samples; and f. subsequent filtering the contaminant in such air samples after the step of coarsely filtering.

14. A method for detecting biological and chemical agents in or on articles, comprising the steps of:

a. moving sealed containers in which articles are disposed;

b. agitating such containers to loosen contaminants which may be contained therein and create a contaminated air cloud to increase the concentration of such contaminants in the air in the sealed containers to facilitate air sampling;

c. withdrawing air samples from the sealed containers; and d. sensing contaminants which are located in the air samples;

placing the containers into a reciprocating container holder, releasing those containers which are free of contaminated air to continue downstream for further processing and handling.

\* \* \* \* \*